United States Patent
Zugmaier et al.

(10) Patent No.: US 11,079,381 B2
(45) Date of Patent: Aug. 3, 2021

(54) RISK-STRATIFICATION OF B-PRECURSOR ACUTE LYMPHOBLASTIC LEUKEMIA PATIENTS

(71) Applicants: AMGEN RESEARCH (MUNICH) GMBH, Munich (DE); AMGEN INC., Thousand Oaks, CA (US)

(72) Inventors: Gerhard Zugmaier, Munich (DE); Peter Kufer, Munich (DE); Shilpa Alekar, San Diego, CA (US)

(73) Assignees: AMGEN RESEARCH (MUNICH) GMBH, Munich (DE); AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/313,136

(22) PCT Filed: May 20, 2015

(86) PCT No.: PCT/IB2015/053705
§ 371 (c)(1),
(2) Date: Nov. 22, 2016

(87) PCT Pub. No.: WO2015/181683
PCT Pub. Date: Dec. 3, 2015

(65) Prior Publication Data
US 2017/0122947 A1   May 4, 2017

Related U.S. Application Data

(60) Provisional application No. 62/005,560, filed on May 30, 2014.

(51) Int. Cl.
| | | |
|---|---|---|
| *C07K 16/28* | (2006.01) | |
| *G01N 33/574* | (2006.01) | |
| *G01N 33/50* | (2006.01) | |
| *A61K 35/17* | (2015.01) | |
| *A61K 38/17* | (2006.01) | |
| *A61K 35/12* | (2015.01) | |

(52) U.S. Cl.
CPC ....... *G01N 33/57426* (2013.01); *A61K 35/17* (2013.01); *A61K 38/1774* (2013.01); *C07K 16/2803* (2013.01); *C07K 16/2809* (2013.01); *G01N 33/5091* (2013.01); *A61K 2035/124* (2013.01); *C07K 2317/31* (2013.01); *C07K 2317/622* (2013.01); *G01N 2333/70503* (2013.01); *G01N 2800/50* (2013.01); *G01N 2800/52* (2013.01); *G01N 2800/56* (2013.01)

(58) Field of Classification Search
CPC .............................. C07K 16/28; G01N 33/574
USPC ..................................................... 424/135.1
See application file for complete search history.

(56) References Cited

FOREIGN PATENT DOCUMENTS

| WO | WO-1999/054440 A1 | 10/1999 |
|---|---|---|
| WO | WO-2004/106381 A1 | 12/2004 |
| WO | WO-2007/068354 A1 | 6/2007 |
| WO | WO-2007/131092 A2 | 11/2007 |
| WO | WO-2008/119565 A2 | 10/2008 |
| WO | WO-2008/119566 A2 | 10/2008 |
| WO | WO-2008/119567 A2 | 10/2008 |
| WO | WO-2010/052014 A1 | 5/2010 |
| WO | WO-2011/051307 A1 | 5/2011 |
| WO | WO-2012/146394 A1 | 11/2012 |

OTHER PUBLICATIONS

Hoelzer et al. (Blood Reviews, 2012, 26: 25-32).*
Background information for the pediatric subcommittee of the oncologic drugs advisory committee meeting, <http://www.fda.gov/downloads/AdvisoryCommittees/CommitteesMeetingMaterials/Drugs/OncologicDrugsAdvisoryCommittee/UCM330210.pdf>, retrieved Jul. 17, 2015.
Bader et al., Prognostic value of minimal residual disease quantification before allogeneic stem-cell transplantation in relapsed childhood acute lymphoblastic leukemia: the ALL-REZ BFM Study Group. *J. Clin. Oncol.* 27: 377-84 (2009).
Basso et al., Risk of relapse of childhood acute lymphoblastic leukemia is predicted by flow cytometric measurement of residual disease on Day 15 bone marrow. *J. Clin. Oncol.* 27(31): 5168-74 (2009).
Buerger et al., Diagnostic cerebrospinal fluid examination in children with acute lymphoblastic leukemia: significance of low leukocyte counts with blasts or traumatic lumbar puncture. *J. Clin. Oncol.* 21(2): 184-8 (2003).
Crick, Codon-anticodon pairing: The Wobble hypothesis. *J. Mol. Biol.* 19: 548-55 (1966).
Eckert et al., Prognostic value of minimal residual disease in relapsed childhood acute lymphoblastic leukaemia. *Lancet* 358: 1239-41 (2001).
Grupp et al., Chimeric antifen receptor-modified T cells for acute lymphoid leukemia. *N. Engl. J. Med.* 368(16): 1509-18 (2013).
Hosse et al., A new generation of protein display scaffolds for molecular recognition. *Protein Sci.* 15: 14-27 (2006).
Nagorsen et al., Blinatumomab: A historical perspective. *Pharm. Therapeut.* 136(3): 334-42 (2012).

(Continued)

Primary Examiner — Yan Xiao
(74) *Attorney, Agent, or Firm* — Marshall, Gerstein & Borun LLP

(57) ABSTRACT

The present invention relates to a method for risk-stratifying subjects suffering from B-precursor acute lymphoblastic leukemia (ALL), wherein said subjects are intended for a therapy comprising administration of a CD3 binding domain. Risk-stratification is based on the determination of the amount blast cells in a bone marrow sample from said subject, and/or on the determination of the number of blast cells per 1 µl in a CSF sample from said subject. According to the category into which subjects are risk-stratified, said subjects can be appropriately treated, while their risk of a potential adverse neurological reaction can be reduced or even excluded.

8 Claims, No Drawings

Specification includes a Sequence Listing.

(56) References Cited

OTHER PUBLICATIONS

Needleman et al., A general method applicable to the search for similarities in the amino acid sequence of two proteins. *J. Mol. Biol.* 48: 443-53 (1970).
Nicaise et al., Affinity transfer by CDR grafting on a nonimmunogloblin scaffold. *Protein Sci.* 13: 1882-91 (2004).
Nygren et al., Scaffolds for engineering novel binding sites in proteins. *Curr. Opin. Struct. Biol.* 7: 463-9 (1997).
Porter et al., Chimeric antigen receptor-modified T cells in chronic lymphoid leukemia. *N. Engl. J. Med.* 365: 725-33 (2011).
Skerra, Alternative non-antibody scaffolds for molecular recognition. *Curr. Opin. Biotechnol.* 18: 295-304 (2007).
Smith et al., Comparison of biosequences. *Adv. Appl. Math.* 2: 482-9 (1981).
Stary et al., Results of the randomized I-BFM-SG trial—Acute lymphoblastic leukemia intercontinental-BFM 2002—in 5060 children diagnosed in 15 countries on 3 continents. <https://ash.confex.com/ash/2011/webprogram/Paper40820.html>, retrieved Jul. 17, 2015.
Tallen et al., Long-term outcome in children with relapsed acute lymphoblastic leukemia after time-point and site-of-relapse stratification and intensified short-course multidrug chemotherapy: Results of trial ALL-REZ BFM 90. *J. Clin. Oncol.* 28(14): 2339-47 (2010).
Visser et al., Prognostic value of day 14 blast percentage and the absolute blast index in bone marrow of children with acute lymphoblastic leukemia. *Pediat. Hematol. Oncol.* 18(3): 187-91 (2001).
International Search Report issued in connection with International Application No. PCT/IB2015/053705, dated Oct. 19, 2015.
Bargou et al., Tumor Regression in Cancer Patients by Very Low Doses of a T-Cell Engaging Antibody, *Science* 321: 974-977 (2008).
Kantarijan et al., Results of Inotzumab Ozogamicin, a CD22 Monoclonal Antibody, in Refractory and Relapsed Acute Lymphocytic Leukemia, *Cancer* 728-736 (2013).
Topp et al., Phase II Trial of the Anti-CD19 Bispecific T Cell—Engager Blinatumomab Shows Hematologic and Molecular Remissions in Patients With Relapsed or Refractory B-Precursor Acute Lymphoblastic Leukemia, *Journal of Clinical Oncology* 22(36): 4134-4142 (2014).
U.S. Food and Drug Administration, Drug Approval Package for Blincyto (blinatumomab) Injection, retrieved from Internet at: <https://wwww.accessdata.fda.gov/drugsatfda_docs/nda/2014/125557Orig1s000TOC.cfm> on Jun. 29, 2020.

\* cited by examiner though it is known that a medicament can cause adverse effects, its prescription and administration could not be avoided or is accepted, since the medicament has an outstanding beneficial therapeutic effect or may even be lifesaving.

SEQUENCE LISTING

<160> NUMBER OF SEQ ID NOS: 23

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

```
Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
            195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
            275                 280                 285

Met His Trp Val Lys Gln Arg Pro Gly Gln Gly Leu Glu Trp Ile Gly
290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
            355                 360                 365

Thr Leu Thr Val Ser Ser Val Glu Gly Gly Ser Gly Gly Ser Gly Gly
            370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
            435                 440                 445

Val Pro Tyr Arg Phe Ser Gly Ser Gly Ser Gly Thr Ser Tyr Ser Leu
            450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys
```

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc    60

```
atctcctgca aggccagcca aagtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg gagggaccaa gctcgagatc aaaggtggtg gtggttctgg cggcggcggc    360
tccggtggtg gtggttctca ggtgcagctg cagcagtctg ggctgagct ggtgaggcct    420 gggtcctcag tgaagatttc ctgcaaggct tctggctatg cattcagtag ctactggatg    480
aactgggtga agcagaggcc tggacagggt cttgagtgga ttggacagat ttggcctgga    540
gatggtgata ctaactacaa tggaaagttc aagggtaaag ccactctgac tgcagacgaa    600
tcctccagca cagcctacat gcaactcagc agcctagcat ctgaggactc tgcggtctat    660
ttctgtgcaa gacgggagac tacgacggta ggccgttatt actatgctat ggactactgg    720
ggccaaggga ccacggtcac cgtctcctcc ggaggtggtg gatccgatat caaactgcag    780
cagtcagggg ctgaactggc aagacctggg gcctcagtga agatgtcctg caagacttct    840
ggctacacct ttactaggta cacgatgcac tgggtaaaac agaggcctgg acagggtctg    900
gaatggattg gatacattaa tcctagccgt ggttatacta attacaatca gaagttcaag    960
gacaaggcca cattgactac agacaaatcc tccagcacag cctacatgca actgagcagc    1020
ctgacatctg aggactctgc agtctattac tgtgcaagat attatgatga tcattactgc    1080
cttgactact ggggccaagg caccactctc acagtctcct cagtcgaagg tggaagtgga    1140
ggttctggtg aagtggagg ttcaggtgga gtcgacgaca ttcagctgac ccagtctcca    1200
gcaatcatgt ctgcatctcc aggggagaag gtcaccatga cctgcagagc cagttcaagt    1260
gtaagttaca tgaactggta ccagcagaag tcaggcacct cccccaaaag atggatttat    1320
gacacatcca aagtggcttc tggagtccct tatcgcttca gtggcagtgg gtctgggacc    1380
tcatactctc tcacaatcag cagcatggag gctgaagatg ctgccactta ttactgccaa    1440
cagtggagta gtaacccgct cacgttcggt gctgggacca agctggagct gaaa           1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110
```

Tyr Trp Gly Gln Gly Thr Thr Val Thr Val Ser Ser
            115                 120

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4
caggtgcagc tgcagcagtc tggggctgag ctggtgaggc ctgggtcctc agtgaagatt     60
tcctgcaagg cttctggcta tgcattcagt agctactgga tgaactgggt gaagcagagg    120
cctggacagg gtcttgagtg gattggacag atttggcctg agatggtgaa tactaactac    180
aatgaaaagt tcaagggtaa agccactctg actgcagacg aatcctccag cacagcctac    240
atgcaactca gcagcctagc atctgaggac tctgcggtct atttctgtgc aagacgggag    300
actacgacgg taggccgtta ttactatgct atggactact ggggccaagg gaccacggtc    360
accgtctcct cc                                                        372

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6
gatatccagc tgacccagtc tccagcttct ttggctgtgt ctctagggca gagggccacc     60
atctcctgca aggccagcca aagtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300

```
acgttcggtg agggaccaa gctcgagatc aaa                    333
```

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8

```
gatatcaaac tgcagcagtc aggggctgaa ctggcaagac ctggggcctc agtgaagatg    60
tcctgcaaga cttctggcta cacctttact aggtacacga tgcactgggt aaaacagagg   120
cctggacagg gtctggaatg gattggatac attaatccta gccgtggtta tactaattac   180
aatcagaagt tcaaggacaa ggccacattg actacagaca atcctccag cacagcctac   240 atgcaactga gcagcctgac atctgaggac tctgcagtct attactgtgc aagatattat   300
gatgatcatt actgccttga ctactggggc caaggcacca ctctcacagt ctcctca     357
```

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60
```

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10
gacattcagc tgacccagtc tccagcaatc atgtctgcat ctccagggga gaaggtcacc     60
atgacctgca gagccagttc aagtgtaagt tacatgaact ggtaccagca gaagtcaggc    120
acctccccca aaagatggat ttatgacaca tccaaagtgg cttctggagt cccttatcgc    180
ttcagtggca gtgggtctgg gacctcatac tctctcacaa tcagcagcat ggaggctgaa    240
gatgctgcca cttattactg ccaacagtgg agtagtaacc cgctcacgtt cggtgctggg    300
accaagctgg agctgaaa                                                  318

<210> SEQ ID NO 11
<211> LENGTH: 10
<212> TYPE: PRT
<213> ORGANISM: artificial
<220> FEATURE:
<223> OTHER INFORMATION: CD3 CDR-H1

<400> SEQUENCE: 11

Gly Tyr Thr Phe Thr Arg Tyr Thr Met His
1               5                   10

<210> SEQ ID NO 12
<211> LENGTH: 17
<212> TYPE: PRT
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:

<223> OTHER INFORMATION: CD3 CDR-L1

<400> SEQUENCE: 14

Arg Ala Ser Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1

<400> SEQUENCE: 17

Gly Tyr Ala Phe Ser Ser Tyr Trp Met Asn
1               5                   10

<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial

```
<220> FEATURE:
<223> OTHER INFORMATION: CD19 CDR-L1

<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Peptide Spacer

<400> SEQUENCE: 23

Gly Gly Gly Gly Ser
1               5
```

RISK-STRATIFICATION OF B-PRECURSOR ACUTE LYMPHOBLASTIC LEUKEMIA PATIENTS

FIELD OF THE INVENTION

The present invention relates to a method for risk-stratifying subjects suffering from B-precursor acute lymphoblastic leukemia (ALL), wherein said subjects are intended for a therapy comprising administration of a CD3 binding domain. Risk-stratification is based on the determination of the amount of blast cells in a bone marrow sample from said subject, and/or on the determination of the number of blast cells per 1 µl in a cerebro—spinal fluid (CSF) sample from said subject. According to the amount of blast cells in a bone marrow sample and/or the number of blast cells in a CSF sample the risk-stratification allows a classification of subjects suffering from B-precursor ALL into categories of subjects who may or may not be at a risk of developing a potential adverse neurological reaction after administration of a CD3 binding domain. According to the category, said subjects can be appropriately treated, while their risk of a potential adverse neurological reaction can be reduced or even excluded.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

BACKGROUND OF THE INVENTION

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. Alternatively, a target antigen may be restricted to a certain lineage of normal cells and cancer cells derived therefrom, wherein the depletion of target antigen-positive normal cells is tolerable e.g. because of their recovery from target antigen-negative stem cells. These situations provide the basis for a therapeutic window in which a defined amount of the antibody-based therapeutic effectively hits cancer cells but spares normal cells.

Though antibodies are an effective means in treating many disorders, in particular cancer, their administration is not necessarily devoid of side effects. Adverse effects may cause a reversible or irreversible change in the health status of a patient. As adverse effects could be harmful and undesired, it is highly desirable to avoid them. However, though it is known that a medicament can cause adverse effects, its prescription and administration could not be avoided or is accepted, since the medicament has an outstanding beneficial therapeutic effect or may even be lifesaving.

In clinical trials, a general distinction can be made between adverse effects (AEs) and serious adverse effects (SAEs). Specifically, adverse effects can be classified in 5 grades in accordance with the Common Terminology Criteria for Adverse Events (CTCAE) version 4. Grade 1 relates to mild AE, Grade 2 to moderate AE, Grade 3 to severe AE, Grade 4 to life-threatening or disabling AE, while Grade 5 means death related to AE.

An adverse effect observed in antibody therapy is the occurrence of infusion-related side effects, such as the cytokine release syndrome ("CRS"). Other adverse side effects described to be associated with CRS are fatigue, vomiting, tachycardia, hypertension, back pain, but also central nervous system neurological reactions (CNS reactions), such as seizures, encephalopathy, cerebral edema, aseptic meningitis, and headache.

Cytokine release and neurological reactions have not only been observed with monoclonal antibodies binding to the T cell receptor but also with a CD19×CD3 bispecific single chain antibody binding to the CD3 part of the T cell receptor (called Blinatumomab (MT103) or AMG 103).

Blinatumomab is a B cell malignancy—directed, recombinant bispecific single-chain CD19×CD3 antibody that binds to CD19 on the surface of almost all B cells and B tumor cells and concomitantly can engage a T cell, thereby triggering the T-cell to kill the target B cell or B tumor cell. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for the CD3 complex on T cells. Blinatumomab is designed to direct the body's cytotoxic, or cell-destroying, T cells against tumor cells, and represent a new therapeutic approach to cancer therapy. Blinatumomab is presently in clinical trials.

As described for instance in WO 99/54440, adverse effects have been observed in a previous study performed with Blinatumomab applied in repeated bolus infusions to a patient with B-cell derived chronic lymphatic leukaemia (B-CLL). In order to try to better manage these undesired side effects, the mode of administration of the CD19×CD3 bispecific single chain antibody has been changed in that it has been switched over from bolus infusion to a continuous intravenous administration of said antibody for a longer period of time. Though pharmaceutical means and methods which allow a more gradual activation of T cell populations (see WO 2007/068354) already helped to avoid significant adverse side effects in patients treated with the CD19×CD3 bispecific single chain antibody, neurological reactions could unfortunately not be prevented by these measures, in particular in cases in which doses of more than 5 to 10 microgram per square meter per day (i.e. 24 h) of the antibody have been administered.

WO 2011/051307 describes that those patients, to whom a CD19×CD3 bispecific antibody was administered, encountered CNS events, if they had a B:T cell ratio of about 1:5 or lower. Accordingly, WO 2011/051307 provides appropriate dosage regimens in order to reduce potential CNS events. WO 2012/146394 established that a total B cell count of less than about 50 B cells per microliter of peripheral blood as indicator for a risk of potential adverse neurological events and thus provides appropriate dosage regimens which help to reduce or even avoid such adverse events.

However, though a low B:T cell ratio and/or a low number of total B cells in peripheral blood has been established as a risk profile associated with an increased risk of CNS-related adverse events when subjects are treated with a CD3 binding domain such as a CD19×CD3 bispecific single chain antibody, e.g. blinatumomab, in combating against lymphoma or leukemia, such a risk profile did not yet turn out to be non-varying when treating subjects suffering from acute lymphoblastic leukemia (ALL). However, "non-varying" does not mean that the thus far established risk profile described in WO 2011/051307 or WO 2012/146394 for subjects suffering from lymphoma is not applicable to subjects suffering from ALL—indeed, it is applicable—but, it turned out in clinical trials that this risk profile can be improved in order to even exclude a potential adverse event, particularly an adverse neurological reaction.

Thus, the technical problem underlying the present invention is to provide means and methods for treating subjects suffering from ALL with a CD3 binding domain while reducing or even excluding the risk of a potential adverse neurological reaction for said subject.

The present invention addresses this need and thus provides methods for risk-stratifying subjects suffering from B-precursor acute lymphoblastic leukemia (ALL) and intended for a therapy which therapy comprises re-directing of T-cells against target cells as well as methods and uses which apply a therapy comprising re-directing of T-cells against target cells for the treatment of B—precursor ALL in a subject that was preferably risk-stratified in accordance with the teaching of the present invention as well as embodiments pertaining to said methods and uses.

As further aspects, the present invention provides the use of a bone marrow sample from a subject suspected to or having B-precursor ALL for predicting the risk of developing a potential adverse neurological reaction, use of a CSF sample from a subject suspected to have or having B—precursor ALL for predicting the risk of developing a potential adverse neurological reaction, use of the amount of blast cells in a bone marrow sample of a subject suspected or having B
 precursor ALL for predicting the risk of developing a potential adverse neurological reaction, use of the number of blast cells in a CSF sample of a subject suspected to have or having B
 precursor ALL for predicting the risk of developing a potential adverse neurological reaction a method for predicting the risk of developing a potential adverse neurological reaction of a subject having B-precursor ALL, comprising determining the amount of blast cells in a bone marrow sample from a subject, and
a method for predicting the risk of developing a potential adverse neurological reaction of a subject having B-precursor ALL, comprising determining the number of blast cells in a CSF sample from a subject,
as well as embodiments pertaining to said uses and methods.

These aspects and embodiments are characterized and described herein and reflected in the claims.

SUMMARY OF THE INVENTION

In a first aspect, the present invention provides a method for risk-stratifying a subject suffering from B-precursor acute lymphoblastic leukemia (ALL), said subject being intended for a therapy which therapy comprises re-directing of T-cells against target cells, the method comprising
(a) determining (preferably ex vivo) the amount of blast cells in a bone marrow sample from said subject; and/or determining (preferably ex vivo) the number of blast cells contained in (per) 1 µl CSF sample from said subject,
(b) risk-stratifying said subject into one of the following categories:

(i) subjects having an amount of at least 20% blast cells per 200 bone marrow cells;
(ii) subjects having 5 blast cells or less per 1 µl CSF;
(iii) subjects having an amount of about less than 20% blast cells per 200 bone marrow cells and 5 or less blast cells per 1 µl CSF;
(iv) subjects having an amount of about less than 20% blast cells per 200 bone marrow cells;
(v) subjects having more than 5 blast cells per 1 µl CSF; or
(vi) subjects having an amount of about less than 20% blast cells per 200 bone marrow cells and more than 5 blast cells per 1 µl CSF.

In one embodiment of the method for risk-stratifying subjects suffering from B-precursor acute lymphoblastic leukemia (ALL),
(i) an amount of at least 20% blast cells per 200 counted bone marrow cells in a bone marrow sample from said subject is indicative for a reduced or no risk of a potential adverse neurological reaction for said subject when being subjected to a therapy which comprises re-directing of T-cells against target cells;
(ii) a number of 5 or less blast cells per 1 µl in a CSF sample from said subject is indicative for a reduced or no risk of a potential adverse neurological reaction for said subject when being subjected to a therapy which comprises re-directing of T-cells against target cells;
(iii) an amount of about less than 20% blast cells per 200 counted bone marrow cells in a bone marrow sample, while concomitantly a number of 5 or less blast cells per 1 µl in a CSF sample from said subject is indicative for a reduced or no risk of a potential adverse neurological reaction for said subject when being subjected to a therapy which comprises re-directing of T-cells against target cells;
(iv) an amount of about less than 20% blast cells per 200 counted bone marrow cells in a bone marrow sample from said subject is indicative for an increased risk of a potential adverse neurological reaction for said subject when being subjected to a therapy which comprises re-directing of T-cells against target cells;
(v) a number of more than 5 blast cells per 1 µl in a CSF sample from said subject is indicative for an increased risk of a potential adverse neurological reaction for said subject when being subjected to a therapy which comprises re-directing of T-cells against target cells; or
(vi) an amount of about less than 20% blast cells per 200 counted bone marrow cells in a bone marrow sample, while concomitantly a number of more than 5 blast cells per 1 µl in a CSF sample from said subject is indicative for an increased risk of a potential adverse neurological reaction for said subject when being subjected to a therapy which comprises re-directing of T-cells against target cells.

In one embodiment, it is envisaged that subjects of categories (v) and (vi) as risk-stratified with the method for risk-stratification of the present invention are to be subject of intrathecal chemotherapy prior to treatment with a therapy which comprises re-directing of T-cells against target cells.

In another embodiment, it is envisaged that subjects of category (i) as risk-stratified with the method for risk-stratification of the present invention are to be subject of a chemotherapy and/or cortisone treatment prior to treatment with a therapy which comprises re-directing of T-cells against target cells, if said subjects have an amount of blasts of more than 50%.

In one embodiment, the risk-stratification allows for the prediction as to whether or not a subject will develop a potential adverse neurological reaction.

In another embodiment, the risk-stratification allows for the mitigation of a potential adverse neurological reaction.

In a second aspect, the present invention provides for a therapy which comprises re-directing of T-cells against target cells for use in a method for treating B-precursor ALL in a subject, said subject is
(a) a subject having 5 or less blast cells per 1 µl in a CSF sample from said subject,
(b) a subject having an amount of 20% or more blast cells per 200 counted bone marrow cells in a bone marrow sample from said subject; or
(c) a subject having an amount of less than 20% blast cells per 200 counted bone marrow cells in a bone marrow sample from said subject and having 5 or less blast cells per 1 µl in a CSF sample from said subject.

In a third aspect, the present invention relates to a method of treating B-precursor ALL in a subject, comprising subjecting a subject in need thereof to a therapy which comprises re-directing of T-cells against target cells, said subject is
(a) a subject having 5 or less blast cells per 1 µl in a CSF sample from said subject,
(b) a subject having an amount of at least 20% blast cells per 200 counted bone marrow cells in a bone marrow sample from said subject; or
(c) a subject having an amount of less than 20% blast cells per 200 counted bone marrow cells in a bone marrow sample from said subject and having 5 or less blast cells per 1 µl in a CSF sample from said subject.

In one embodiment of the second and third aspect, a neurological reaction is one or more selected from the group consisting of: confusion, ataxia, disorientation, dysphasia, aphasia, speech impairment, cerebellar symptoms, tremor, apraxia, seizure, grand mal convulsion, palsy, and balance disorder.

In one embodiment of the second and third aspect, said therapy which comprises re-directing of T-cells against target cells in a patient, includes a CD3 binding domain.

In a preferred embodiment of the second and third aspect, a CD3 binding domain is a bispecific single chain antibody, preferably a CD19×CD3 bispecific single chain antibody. The preferred CD19×CD3 bispecific single chain antibody is blinatumomab (AMG 103).

In another embodiment of the second and third aspect, said therapy which comprises re-directing of T-cells against target cells in a subject includes an genetically engineered T-cell having a chimeric antigen receptor (CAR).

In one embodiment of the second and third aspect, respectively, the subject is a human.

In a further aspect, the present invention relates to the use of a bone marrow sample from a subject suspected to or having B-precursor ALL for predicting the risk of developing a potential adverse neurological reaction, wherein an amount of at least 20% blast cells per 200 counted bone marrow cells in a bone marrow sample of said subject is indicative for a reduced or no risk of a potential adverse neurological reaction for said subject.

In another aspect, the present invention provides for a method for predicting the risk of developing a potential adverse neurological reaction of a subject having B-precursor ALL, comprising determining the amount of blast cells in a bone marrow sample from a subject, wherein an amount of at least 20% blast cells per 200 counted bone marrow cells in a bone marrow sample of said subject is indicative for a reduced or no risk of a potential adverse neurological reaction for said subject.

In a still further aspect, the present invention concerns the use of the amount of blast cells in a bone marrow sample of a subject suspected or having B-precursor ALL for predicting the risk of developing a potential adverse neurological reaction, wherein an amount of at least 20% blast cells per 200 counted bone marrow cells in a bone marrow sample of said subject is indicative for a reduced or no risk of a potential adverse neurological reaction for said subject.

In a yet further aspect, the present invention encompasses the use of a CSF sample from a subject suspected to have or having B-precursor ALL for predicting the risk of developing a potential adverse neurological reaction, wherein 5 or less blast cells per 1 µl in a CSF sample from said subject is indicative for a reduced or no risk of a potential adverse neurological reaction for said subject.

In another aspect, the present invention provides for the use of the number of blast cells in a CSF sample of a subject suspected to have or having B-precursor ALL for predicting the risk of developing a potential adverse neurological reaction, wherein a number of 5 or less blast cells per 1 µl in a CSF sample of said subject is indicative for a reduced or no risk of a potential adverse neurological reaction for said subject.

In still another aspect, the present invention relates to a method for predicting the risk of developing a potential adverse neurological reaction of a subject having B-precursor ALL, comprising determining the number of blast cells in a CSF sample from a subject, wherein a number of 5 or less blast cells per 1 µl in a CSF sample of said subject is indicative for a reduced or no risk of a potential adverse neurological reaction for said subject.

DETAILED DESCRIPTION OF THE INVENTION

The present inventors observed that presence of target cells, which are combated by a therapy which comprises re-directing of T-cells against target cells, whereby T cells can be re-directed, e.g. by a CD3 binding domain or by a chimeric antigen receptor (CAR), in the central nervous system (CNS) as well as lack of peripheral B cells could result in adverse neurological reaction in a subject suffering from B-precursor ALL which is treated by way of such a therapy. Namely, without being bound by theory, a therapy which includes re-directing T against lymphoblastic leukemia target cells could lead to potential adverse neurological reactions in that re-directed T cells adhere to blood vessel endothelium, activate the endothelium, start to extravasate and migrate even into the CNS. It is assumed that activated endothelial cells attract other peripheral blood leukocytes e.g. monocytes which in turn may cause transient neuroinflammation and perturbation of the blood CSF-barrier. Perturbation of the blood CSF-barrier caused by endothelial stress due to adhesion of re-directed T cells and activation of endothelial cells is assumed to result in leakage of the blood cerebrospinal fluid (CSF) barrier and thus allows diffusion and migration of effector cells, e.g., T cells engaged by a CD3 binding domain or CAR-modified T cells (see e.g. Grupp et al. (2013), N. Engl. J. Med. 368 (16), pp. 1509-1518) and/or diffusion of a CD3 binding domain into the CSF. It is known that subjects suffering from acute lymphoblastic leukemia have leukemic cells such as blast cells in the CSF (see e.g. Buerger et al. (2003), Journal of Clinical Oncology 21, No 2, pp. 184-188. When a re-directed T cell will encounter a target cell, such as a blast cell in the CSF and will kill the target cell, the T cell will also become activated and thus attracts further effector cell and triggers, e.g., cytokine production. One or more of these events are assumed to contribute to neuroinflammation and/or toxic effects on neuronal cells of soluble factors such as cytokines which could then result in the development of an adverse neurological reaction.

Accordingly, having observed in clinical trials the above, the present inventors figured out that the amount of blast cell in a bone marrow sample from a subject suffering from B-precursor ALL and/or the number of blast cells in a CSF sample from said subject are suitable prognostic parameters that are to be taken into account in the treatment of B-precursor ALL.

Specifically, the present inventors found that an amount of about less than 20% blast cells per 200 counted bone marrow cells in a bone marrow sample from a subject suffering from B-precursor ALL is indicative for an increased risk of a potential adverse neurological reaction for said subject when being subjected to a therapy which comprises re-directing of T-cells against target cells, whereas an amount of at least 20% blast cells per 200 counted bone marrow cells in a bone marrow sample from a subject suffering from B-precursor ALL is indicative for a reduced or no risk of a potential adverse neurological reaction for said subject when being subjected to a therapy which comprises re-directing of T-cells against target cells.

Also, the present inventors found that than 5 blast cells per 1 µl in a CSF sample from said subject is indicative for an increased risk of a potential adverse neurological reaction for said subject when being subjected to a therapy which comprises re-directing of T-cells against target cells, whereas 5 or less blast cells per 1 µl in a CSF sample from said subject is indicative for a reduced or no risk of a potential adverse neurological reaction for said subject when being subjected to a therapy which comprises re-directing of T-cells against target cells.

Hence, the present inventors, so to say, determined two risk factors for subjects suffering from B-precursor ALL (sometimes herein also called "ALL patients") that should ideally be checked before a CD3 binding domain will be administered to said subjects—amount of blast cells in a bone marrow sample and/or number of blast cells in a CSF sample. This finding came as a surprise for the present inventors, since thus far the risk factor—lack of protective B cells—could thus far only be reliably established in Non-Hodgkin lymphoma (NHL) treatment with a therapy which comprises re-directing of T-cells against target cells, but not in B-precursor ALL treatment with such a therapy. The most likely explanation for this may be based on the fact that bone marrow infiltration by leukemic B cells plays a much bigger role in B-precursor ALL than in NHL.

The finding of the present inventors therefore paves the way for risk-stratifying subjects suffering from B-precursor ALL, whereby said subjects are intended for a a therapy which comprises re-directing of T-cells against target cells into categories of subjects who may or may not be at a risk of potential adverse neurological reactions. Notably, even though subjects may be at such a risk, the present invention teaches what to do in order to have a much reduced or ideally no such risk. Accordingly, the findings of the present inventors also pave the way for treating B-precursor ALL with a therapy which comprises re-directing of T-cells against target cells, while concomitantly reducing or even eliminating the risk of potential adverse neurological reactions. Thus, the present invention much contributes to an B-precursor ALL therapy with a therapy which comprises re-directing of T-cells against target cells which is ideally free of adverse neurological reactions.

For the avoidance of any doubt, it is hereby stressed that the disclosure of the present invention including all definitions etc. is fully applicable to all embodiments that form part of the present invention (i.e. are linked with the gist of the invention and therefore fall into the context of the present invention), irrespective of whether these embodiments are drafted as method for risk-stratifying subjects embodiments, use or methods of treatment embodiments or use or method embodiments, etc. Thus, all definitions and embodiments can be used and apply to all embodiments disclosed herein.

Definitions

It must be noted that as used herein, the singular forms "a", "an" and "the" include plural references and vice versa unless the context clearly indicates otherwise. Thus, for example, a reference to "a host cell" or "a method" includes one or more of such host cells or methods, respectively, and a reference to "the method" includes equivalent steps and methods that could be modified or substituted known to those of ordinary skill in the art. Similarly, for example, a reference to "methods" or "host cells" includes "a host cell" or "a method", respectively.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term". For example, A, B and/or C means A, B, C, A+B, A+C, B+C and A+B+C.

Throughout this specification and the claims or items, unless the context requires otherwise, the word "comprise" and variations such as "comprises" and "comprising" will be understood to imply the inclusion of a stated integer (or step) or group of integers (or steps). It does not exclude any other integer (or step) or group of integers (or steps). When used herein, the term "comprising" can be substituted with "containing", "composed of", "including", "having" or "carrying." When used herein, "consisting of" excludes any integer or step not specified in the claim/item. When used herein, "consisting essentially of" does not exclude integers or steps that do not materially affect the basic and novel characteristics of the claim/item. In each instance herein any of the terms "comprising", "consisting essentially of" and "consisting of" may be replaced with either of the other two terms.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

It should be understood that this invention is not limited to the particular methodology, protocols, material, reagents, and substances, etc., described herein. The terminologies used herein are for the purpose of describing particular embodiments only and are not intended to limit the scope of the present invention, which is defined solely by the claims/items.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

In a first aspect the present invention provides a method for risk-stratifying subjects suffering from B-precursor acute lymphoblastic leukemia (ALL), said subjects are intended for a therapy comprising re-directing of T-cells against target cells, comprising
(a) determining the amount of blast cells in a bone marrow sample from said subject; and/or determining the number of blast cells per 1 µl in a CSF sample from said subject,
(b) risk-stratifying said subjects into one of the following categories:
  (i) subjects having an amount of at least 20% blast cells per 200 counted bone marrow cells in a bone marrow sample from said subjects;
  (ii) subjects having 5 blast cells or less per 1 µl in a CSF sample from said subjects;
  (iii) subjects having an amount of about less than 20% blast cells per 200 counted bone marrow cells in a bone marrow sample from said subjects, while said subjects having 5 or less blast cells per 1 µl in a CSF sample from said subjects;
  (iv) subjects having an amount of about less than 20% blast cells per 200 counted bone marrow cells in a bone marrow sample from said subjects;
  (v) subjects having more than 5 blast cells per 1 µl in a CSF sample from said subjects; or
  (vi) subjects having an amount of about less than 20% blast cells per 200 counted bone marrow cells in a bone marrow sample from said subjects, while said subjects having more than 5 blast cells per 1 µl in a CSF sample from said subjects.

The terms "risk-stratifying" and "risk-stratification" as used herein means that subjects are identified on the basis of molecular, biochemical, anatomical and/or histological testing and accordingly assigned or classified into categories of subjects with the aim of selecting the optimal management for the subjects and achieve the best possible outcome in terms of risk management and achievement of the optimal treatment outcome, here particularly treatment of B-precursor ALL in an ideal scenario without a risk of potential adverse neurological reactions. The classification is dependent on the amount of blast cells per 200 counted bone marrow cells in a bone marrow from an individual subject and/or dependent on the number of blast cells in a CSF sample from an individual subject. The amount of blast cells in a bone marrow sample and/or the number of blast cells in a CSF sample indicate whether or not a subject may be at a reduced or no risk for a potential adverse neurological reaction or may be at an increased risk for a potential adverse neurological reaction. Accordingly, a certain category to which a subject is assigned reflects, so to say, the probability for a risk of experiencing an adverse neurological reaction when a subject is treated with a therapy which comprises re-directing of T-cells against target cells.

The method for risk-stratifying subjects allows thus in a preferred embodiment for the (risk) prediction as to whether or not a subject will develop a potential adverse neurological reaction. Similarly, the method for risk-stratifying subjects allows in a preferred embodiment for the mitigation of a potential adverse neurological reaction.

A "cut off" percentage value for the amount of blast cells per 200 counted blast cells in a bone marrow sample from a subject is about 20%. Less than 20% blast cells in said bone marrow sample is indicative for an increased risk of a potential adverse neurological reaction for said subject when being subjected to a therapy which comprises re-directing of T-cells against target cells, while at least 20% blast cells in said bone marrow sample is indicative for a reduced or no risk of a potential adverse neurological reaction for said subject when being subjected to a therapy which comprises re-directing of T-cells against target cells.

The term "about" or "approximately" as used herein in the context of the percentage value of blast cells in a bone marrow sample means within 10%, preferably within 5%, and more preferably within 5% of the given percentage value. It includes also the concrete number, e.g., about 20 includes 20.

The term "or less" or "less than", or the term "or more" or "more than" includes the concrete number. For example, less than 20 means ≤20 and more than 20 means ≥20.

A "cut off" value for the number of blast cells per 1 µl in a CSF sample from a subject is about 5. More than 5 blast cells in said CSF sample is indicative for an increased risk of a potential adverse neurological reaction for said subject when being subjected to a therapy which comprises re-directing of T-cells against target cells, while 5 or less blast cells in said CSF sample is indicative for a reduced or no risk of a potential adverse neurological reaction for said subject when being subjected to a therapy which comprises re-directing of T-cells against target cells.

The term "about" or "approximately" as used herein in the context of the value of blast cells in a CSF sample means within 60%, preferably within 40%, and more preferably within 20% of the given value. It includes also the concrete number, e.g., about 5 includes 5.

The term "or less" or "less than", or the term "or more" or "more than" includes the concrete number. For example, less than 5 means ≤5 and more than 5 means ≥5.

"Acute lymphoblastic leukemia", abbreviated "ALL", when used herein encompasses B-precursor ALL or as is also called B-cell precursor ALL (both terms are also included by the abbreviation "ALL") as well as pediatric or childhood ALL as well as ALL in adults, i.e., adult ALL. B-precursor ALL is the most common type of ALL. Acute lymphoblastic leukemia (ALL) is a form of leukemia, or cancer of the white blood cells characterized by excess lymphoblasts. ALL is, inter alia, characterized by continuously multiplying malignant, immature white blood cells that are overproduced in the bone marrow. ALL causes damage and death by crowding out normal cells in the bone marrow, and by spreading (infiltrating) to other organs. ALL is most common in childhood with a peak incidence at 2-5 years of age, and another peak in old age. "Acute" refers to the relatively short time course of the disease (being fatal in as little as a few weeks if left untreated) to differentiate it from the very different disease of chronic lymphocytic leukemia, which has a potential time course of many years. It is interchangeably referred to as lymphocytic or lymphoblastic. This refers to the cells that are involved, which if they were normal would be referred to as lymphocytes but are seen in this disease in a relatively immature (also termed "blast") state. ALL when referred to herein comprises preferably malignant CD19 positive lymphocytes. B-precursor ALL is, in the context of the present invention, a preferred embodiment of ALL.

"Malignant" describes lymphocytes (in particular B cells) that contribute to a progressively worsening disease, in particular lymphoma or leukemia and the diseases described herein. Malignant CD19 positive lymphocytes (in particular B cells) are not self-limited in their growth, are capable of invading into adjacent tissues, and may be capable of spreading to distant tissues (metastasizing). Malignant when used herein is synonymous with cancerous. WO 2010/052013 provides means and methods for treating pediatric or childhood ALL, particularly refractory and/or relapsed pediatric ALL.

When used herein, pediatric or childhood acute lymphoblastic leukemia (ALL) encompasses pediatric B-lineage ALL, preferably pediatric B-precursor acute lymphoblastic leukemia ALL, more preferably pediatric pro-B ALL, pre-B ALL, or common ALL (cALL). Even more preferred the pediatric B-precursor ALL is common ALL (cALL). Pediatric or childhood acute lymphoblastic leukemia (ALL) also encompasses minimal residual disease (MRD) in a pediatric patient with acute lymphoblastic leukemia (ALL).

The term "refractory pediatric ALL" as used herein means resistance of the pediatric ALL to conventional or standard pediatric ALL therapy, such as chemotherapy and/or HSCT. Currently, the relapse rate in pediatric ALL is about 25%. Put in other words: The conventional or standard pediatric ALL therapy is not able to ultimately cure all pediatric patients.

The term "relapsed pediatric ALL" as used herein denotes the return of signs and symptoms of the ALL disease after a pediatric patient has enjoyed a remission. For example, after conventional ALL treatment using chemotherapy and/or HSCT, a pediatric ALL patient may go into remission with no sign or symptom of the ALL, remains in remission for a couple of years, but then suffers a relapse and has to be treated once again for ALL.

The term "minimal residual disease (MRD)" as defined herein denotes a term used after treatment e.g. with chemotherapeutics when leukemic cells cannot be found in the bone marrow using standard tests, such as microscopic methods. Rather, more sensitive tests such as flow cytometry (FACS based methods) or polymerase chain reaction (PCR) have to be used in order to find evidence that leukemia cells remained in the bone marrow of the pediatric ALL patient. More specifically, the presence of leukemia cells below the cytological detection limit (5% leukemic cells) is defined as minimal residual disease (MRD). If no MRD is detectable (<$10^{-4}$, i.e. less than 1 leukemia cell per $10^4$ bone marrow cells detectable), a complete molecular remission is reached (MRD negativity or MRD negative status). An "MRD positive status" as defined herein means a signal measured by PCR or FACS above detection limit or a quantitative threshold. An "MRD negative status" as defined herein means below detection limit and/or below a quantitative threshold measured by PCR or FACS. The prognostic value of minimal residual disease quantification in childhood ALL has been described e.g. in Bader et al. (J. Clin. Oncol. 27 (2009): 377-384) or Eckert et al. (Lancet 358 (2001): 1239-41). The MRD status can be measured by PCR or FACS analysis in that the individual cytogenetic abnormalities mentioned herein, and/or rearrangements of immunoglobulin genes or T-cell receptor (TCR) rearrangements are quantitatively detected. For example, PCR analysis can detect fusion transcripts such as bcr/abl or t(4; 11) translocations as well as individual clonal rearrangements of immunoglobulins (IgH) and/or T-cell receptor genes (TCR).

WO 2010/052014 provides means and methods for treating adult ALL. "Adult ALL" encompasses lineage acute lymphoblastic leukemia, preferably B-precursor acute lymphoblastic leukemia, ALL which is refractory to chemotherapy in subjects non-eligible for allogeneic hematopoietic stem cell transplantation, as well as minimal residual disease (MRD) in a subject with acute lymphoblastic leukemia (ALL).

A "therapy which comprises re-directing of T-cells against target cells" is to be understood as a therapy, such as a medicament, which is characterized by the appearance and/or existence of "re-directed T-cells", i.e. the therapy either comprises or consists of re-directed T-cells as such, for example genetically engineered T-cell having a chimeric antigen receptor CAR (optionally formulated as a pharmaceutical composition) and/or the re-directed T-cells appear in the course of the therapy exemplified by a medicament which comprises a CD3-specific binding domain as defined herein, preferably a CD3-specific binding domain together with a binding domain which is specific for B-cells, more preferably a CD3-specific binding domain together with a binding domain which is specific for a CD-marker that can be found on B-cell lymphoma such as CD19, CD22, CD20 or CD79a, CD19 being preferred. In a more preferred embodiment, said therapy which comprises re-directing of T-cells against target cells is a therapy with a bispecific CD3×CD19 antibody and in a most preferred embodiment said therapy which comprises re-directing of T-cells against target cells is a therapy with Blinatumomab. Thus, in a particularly preferred embodiment said re-directed T-cell is a human T-cell that has been contacted with (is bound by) Blinatumomab (AMG 103). It is also envisaged that said therapy with Blinatumomab encompasses the administration of 5 to 10 µg/m$^2$/day or higher doses, such as 15, 45 or 60 µg/m$^2$/day. The above mentioned CD-3 specific binding domains are explained in great detail herein elsewhere.

Chimeric antigen receptors (CARs) are fusion proteins comprising antigen recognition moieties and T cell-activation domains. Typically, T cells from a patient are extracted, subjected to chimeric antigen receptor (CAR) cell engineering, and then infused as engineered T cells back into the patient. The engineering, which takes about 10 days, changes the T cell in two ways. First, it adds a receptor that targets the an antigen that is found on most leukemic cells; when the cells are inserted back into the patient's body, they home in on this antigen, latch on and destroy the leukemic cell. Second, the process inserts a viral vector mechanism into the cells which—once the cells have latched on to the leukemia—triggers these T cells to expand and proliferate, so that they seek out and destroy all the remaining leukemic cells.

For the treatment of B cell-malignancies, CD19 CARs consisting of a CD19-specific binding domain linked to, e.g. CD3zeta have been described in clinical studies for B CLL (Porter et al. N Engl J Med. 2011; 365:725-33) and B ALL (Grupp et al. N Engl J Med. 2013). As observed with the infusion of a CD19×CD3 bispecific single-chain antibody, adoptive transfer of CD19 CAR-transduced T cells into patients led to rapid and sustained eradication of normal and malignant B cells. Common adverse events associated with CD19 CAR T cell-therapy included cytokine release syndrome and lymphopenia, but cases of CNS AEs were also reported. Thus, interference with adhesion and transmigration of CD19 CAR T cells to/through blood vessel-lining endothelium also is a useful approach for the prophylaxis and/or amelioration of CD19 CAR T cell-induced CNS AEs. Of note, it is envisaged that treatment with CAR T cells targeting other B cell-specific antigens (e.g. CD20) would also benefit from co-medication with compounds with anti-adhesive properties for the prophylaxis and/or amelioration of CNS AEs caused by such CAR T cells.

The "chimeric antigen receptor (CAR)" as used herein comprises a binding domain which is specific for B-cells, preferably specific for a CD-marker that can be found on B-cell lymphoma such as CD19, CD22, CD20 or CD79a, CD19 being preferred. T-cells that have been genetically engineered to express a chimeric antigen receptor CAR (a T-cell CAR) are exemplified in WO2007/131092. It is meanwhile known that also a therapy comprising T-cell CARs triggers clinical adverse events, and in particular CNS AE.

The present invention also relates to a nucleic acid which encodes a chimeric antigen receptor (CAR) for use in a method of re-directing of T-cells against target cells in a subject as described herein. A nucleic acid sequence thereby includes, although not being limited thereto, vectors etc., which will allow the expression of the desired CARs in T-cells (see for example WO2007/131092 which is included herein by reference).

The term "target cells" is not specifically limited and relates preferably to cancer target cells (in particular cancer cells that express a suitable target which makes them attackable). B-lymphoma cells are more preferred, CD19 positive B-cells (B-lymphoma cells) being most preferred.

The term "subject" includes all mammals, but is not limited to mouse, rat, dog, horse, camel, primates, etc., primates being preferred and human beings being most preferred. In a preferred embodiment the subject is suspected/assumed to comprise or already comprises malignant CD19-positive B cells. In the latter case said patient has already been diagnosed to comprise such cells. The malignant CD19-positive B cells are present in a subject developing and/or suffering from ALL. Preferably, a subject who will be or is treated with a therapy which comprises re-directing of T-cells against target cells is (or has been) risk-stratified in accordance with the method of the first aspect of the invention as described herein. When used herein, the term "subject" is equivalently used with the term "patient". Hence these two terms can be interchangeably used herein. The term "subject" as used herein includes both non-adult and adult human subjects. The term "adult ALL" or "adult ALL patient" or "adult patient" as referred to herein denotes adults aged more than 18 years, i.e. patients aged 19, 20, 21, 22, 23, 24, 25, 30, 35, 40, or 50 years or more. Even patients with 70, 75, 80, 85, 90, 100 years or older may be treated. The term "pediatric ALL" or "childhood ALL" is to be understood as ALL of a pediatric subject aged between 1 month (including 1 month) and 18 years (including 18 years).

Mammalian "endothelial cells" can be isolated from large vessels or capillaries. The term "endothelial cells" thereby includes freshly isolated endothelial cells (for example HUVECs), commercially available endothelial cells from different manufacturers (e.g. PromoCell) and endothelial cell lines, although endothelial cell lines are less preferred. Human endothelial cells are preferred. Human Umbilical Vein Endothelial Cells (HUVEC) and Human Brain Microvascular Endothelial Cells (HBMEC) are particularly preferred, HBMECs being most preferred.

The degree of an adverse effect can, for example, be measured in accordance with the NCI Common Terminology Criteria for Adverse Events v3.0 (CTCAE) (Publish Date: Dec. 12, 2003) in grades. A Grade refers to the severity of the adverse effects. The CTCAE v3.0 displays grades 1 through 5 with unique clinical descriptions of severity for each adverse effectsGrade 1 relates to mild AEs, Grade 2 to moderate AEs, Grade 3 to severe AEs, Grade 4 to life-threatening or disabling AEs, while Grade 5 means death related to AEs. All these AEs are contemplated within the framework of the present invention and included by the term "clinical adverse events" or "adverse effects" or related terms used herein.

The term "clinical adverse events" used herein caused by therapy which comprises re-directing of T-cells against target cells in a patient comprises in particular neurological adverse events. Said neurological adverse event, which sometimes is also denoted as "neurological symptom" or "neurological adverse effect" or "central nervous system adverse event (CNS AE)", includes but is not limited to conditions of a subject, preferably human subject, such as all forms of pain, headache, muscle weakness/incoordination, balance disorder, speech disorder/impairment, sensual disturbance/abnormalities, dizziness, ataxia, apraxia, tremor, aphasia, dysphasia, confusion, disorientation, hallucination, cerebellar symptoms, encephalopathy, seizure, (grand mal) convulsion. Specifically, neurological symptoms observed during treatment with a therapy comprising re-directing of T cells against target cells e.g. through T cell transduction with a CAR or T cell recruitment via a compound comprising a CD3-specific binding domain include for example confusion and disorientation. "Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological symptoms also suffer from loss of memory. Frequently, confusion leads to loss of the ability to recognize people and/or places, or to tell time and date. Feelings of disorientation are common in confusion, and the decision-making ability is impaired. Neurological symptoms further comprise blurred speech and/or word-finding difficulties. This disorder may impair the expression and understanding of language as well as reading and writing. Additionally, vertigo and dizziness may accompany neurological symptoms in some patients.

The term "potential" when used in the context of adverse effects means that—though a subject may have less than 20% blast cells per 200 counted blast cells in a bone marrow sample from said subject and/or more than 5 blast cells in a CSF sample form said subject—said subject does not necessarily have to encounter adverse effects. Accordingly, the term "potential" implies that the method of the first aspect of the present invention provides predictions as to whether or not a subject may encounter adverse effects, but—self-explanatory as it is—cannot provide a 100% safe prediction, since, apart from the amount of blast cells per 200 counted bone marrow cells in a sample from a subject and/or the number of blast cells in a CSF sample from a subject individual factors such as sex, age, weight, nutritional status, health status, pre-medication etc. may have an influence as to whether or not a subject will encounter adverse effects.

As explained herein, the method for risk-stratifying subjects suffering from B-precursor acute lymphoblastic leukemia (ALL) allows risk-stratifying subjects into risk categories dependent on the amount of blast cells in a bone marrow from a subject and/or the number of blast cells in a CSF sample from a subject. Specifically, (i) an amount of at least 20% blast cells per 200 counted bone marrow cells in a bone marrow sample from said subject is indicative for a reduced or no risk of a potential adverse neurological reaction for said subject when being subjected to a therapy which comprises re-directing of T-cells against target cells;

(ii) a number of 5 or less blast cells per 1 µl in a CSF sample from said subject is indicative for a reduced or no risk of a potential adverse neurological reaction for said subject when being subjected to a therapy which comprises re-directing of T-cells against target cells;

(iii) an amount of about less than 20% blast cells per 200 counted bone marrow cells in a bone marrow sample, while concomitantly a number of 5 or less blast cells per 1 µl in a CSF sample from said subject is indicative for a reduced or no risk of a potential adverse neurological reaction for said subject when being subjected to a therapy which comprises re-directing of T-cells against target cells;

(iv) an amount of about less than 20% blast cells per 200 counted bone marrow cells in a bone marrow sample from said subject is indicative for an increased risk of a potential adverse neurological reaction for said subject when being subjected to a therapy which comprises re-directing of T-cells against target cells;

(v) a number of more than 5 blast cells per 1 µl in a CSF sample from said subject is indicative for an increased risk of a potential adverse neurological reaction for said subject when being subjected to a therapy which comprises re-directing of T-cells against target cells; or (vi) an amount of about less than 20% blast cells per 200 counted bone marrow cells in a bone marrow sample, while concomitantly a number of more than 5 blast cells per 1 µl in a CSF sample from said subject is indicative for an increased risk of a potential adverse neurological reaction for said subject when being subjected to a therapy which comprises re-directing of T-cells against target cells.

The term "indicative for" when used in the context of the methods and uses herein means that the amount of blast cell per 200 counted bone marrow cells in a bone marrow sample from a subject and/or a number of blast cells per 1 µl in a CSF sample from a subject are a potential risk factor or risk indicator as to whether or not a subject may have a reduced or no risk for an adverse neurological reaction or may have an increased risk for an adverse neurological reaction, respectively. Thus, the amount of blast cell per 200 counted bone marrow cells in a bone marrow sample from a subject and/or a number of blast cells per 1 µl in a CSF sample from a subject are, so to say, risk-stratification biomarkers.

Subjects of categories (v) and (vi) are in one embodiment preferably subject to intrathecal chemotherapy prior to treatment with the therapy as described herein. This is envisaged in order to reduce the number of blast cells in the CNS or ideally even eliminate blast cells in the CNS, since such blast cells are target cells of the therapy as described herein, whereby destruction of such target cells in the CNS may cause adverse neurological reactions in line with the considerations of the present inventors and the observations from the clinical trials.

Subjects of category (i) are in one embodiment preferably subject to chemotherapy and/or cortisone treatment prior to treatment with the therapy as described herein, if said subjects have an amount of blasts in a bone marrow sample of 50% or more. This is envisaged in order to avoid a potential tumor lysis syndrome.

Based on the findings of the present inventors, it is possible to apply a risk management for subjects suffering from B-precursor ALL with the aim of reducing or even abolishing potential adverse side effects, in particular potential adverse neurological reactions.

Accordingly, in a second aspect, the present invention provides a therapy which comprises re-directing of T-cells against target cells for use in a method for treating B-precursor ALL in a subject, said subject is (a) a subject having 5 or less blast cells per 1 µl in a CSF sample from said subject, (b) a subject having an amount of at least 20% blast cells per 200 counted bone marrow cells in a bone marrow sample from said subject; or (c) a subject having an amount of less than 20% blast cells per 200 counted bone marrow cells in a bone marrow sample from said subject and having 5 or less blast cells per 1 µl in a CSF sample from said subject.

Furthermore, in a third aspect, the present invention provides a method of treating B-precursor ALL in a subject, comprising subjecting a subject in need thereof to a therapy which comprises re-directing of T-cells against target cells, said subject is (a) a subject having 5 or less blast cells per 1 µl in a CSF sample from said subject, (b) a subject having an amount of at least 20% blast cells per 200 counted bone marrow cells in a bone marrow sample from said subject; or (c) a subject having an amount of less than 20% blast cells per 200 counted bone marrow cells in a bone marrow sample from said subject and having 5 or less blast cells per 1 µl in a CSF sample from said subject.

In connection with the present invention a "CD3-specific binding domain" sometimes also denoted herein as "CD3 binding domain" characterizes a binding domain which comprises a framework/framework region and an "antigen-binding site" or an "antigen-interaction site" which is able to specifically interact with a CD3 antigen. Said binding/interaction is also understood to define a "specific recognition". The term "specifically interact/interacting" means in accordance with this invention that the binding domain is capable of binding to at least two, preferably at least three, more preferably at least four amino acids of the CD3 antigen, preferably the CD3epsilon antigen, and more preferably the human CD3epsilon antigen. Such CD3 binding domains as well as specific CD3epsilon epitopes are well-known to the skilled person and exemplified in great detail for example in WO2008119567 or in WO2008119566, both of which are included herein by way of reference thereto.

In one embodiment, a neurological reaction is one or more selected from the group consisting of: confusion, ataxia, disorientation, dysphasia, aphasia, speech impairment, cerebellar symptoms, tremor, apraxia, seizure, grand mal convulsion, palsy, and balance disorder.

In one embodiment, the therapy comprises re-directing of T-cells against target cells in a subject, includes a CD3 binding domain which is preferably a bispecific single chain antibody.

In an alternative or additional embodiment to said therapy comprising re-directing of T-cells against target cells in a subject which includes a CD3 binding domain, said therapy includes an genetically engineered T-cell having a chimeric antigen receptor (CAR).

Said bispecific single chain antibody is preferably a CD19×CD3 bispecific single chain antibody, particularly preferred the CD19×CD3 bispecific single chain antibody is blinatumomab (AMG 103).

In a preferred embodiment, the therapy is for a human.

As used herein, "CD3" denotes a molecule expressed as part of the T cell-receptor complex and has the meaning as typically ascribed to it in the prior art. In humans, it encompasses in individual or independently combined form all known CD3 subunits, for example CD3epsilon, CD3delta, CD3gamma and CD3zeta. The human CD3epsilon antigen is indicated in GenBank Accession No. NM_000733.

A preferred example of a CD3-specific binding domain in line with the present invention is an antibody. The CD3-specific binding domain may be a monoclonal or polyclonal antibody or derived from a monoclonal or polyclonal antibody. The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual", Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2, etc.). The definition of the term "antibody" also includes embodiments such as chimeric, single-chain, de-immunized and humanized antibodies, as well as antibody fragments, like, inter alia, Fab fragments. Antibody fragments or derivatives further comprise F(ab')$_2$, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

The term "framework (region)" includes a scaffold for antigen-binding sites. For example, such a scaffold could be provided by protein A, in particular the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain or thioredoxin (Skerra. *Curr Opin Biotechnol.* 2007; 18:295-304; Hosse et al. *Protein Sci.* 2006; 15:14-27; Nicaise et al. *Protein Sci.* 2004; 13:1882-91; Nygren and Uhlén. *Curr Opin Struct Biol.* 1997; 7:463-9).

In the context of the present invention a preferred framework is the art-recognized portions of an antibody variable region that exist between the more divergent (i.e. hypervariable) complementarity determining regions (CDRs) within the variable region of an antibody. Such framework regions are typically referred to as frameworks 1 through 4 (FR1, FR2, FR3, and FR4) and provide scaffolds for the presentation of the six CDRs (three from the heavy chain and three from the light chain) in three dimensional space, to form an antigen-binding surface.

Bispecific antibody formats are preferred; however, other multispecific antibody formats (trispecific, tetrabodies, etc.) are not excluded. It is preferred that said CD3 binding domain is contained in or is comprised by a bispecific single chain antibody. Said bispecific single chain antibody further comprises in another preferred embodiment of the present invention a binding domain which is specific for B-cells, preferably specific for a CD-marker that can be found on B-cell lymphoma such as CD19, CD22, CD20 or CD79a, CD19 being preferred. In a particularly preferred embodiment, said bispecific single chain antibody is a CD19×CD3 or CD20×CD3 bispecific single chain antibody. In an even more preferred embodiment, said CD19×CD3 bispecific single chain antibody is Blinatumomab (MT103/AMG 103).

In a further preferred embodiment of the present invention said CD19×CD3 bispecific single-chain antibodies comprise a first binding domain capable of binding to an epitope of human CD3epsilon and a second binding domain capable of binding to human CD19. The human CD-Antigens are easily derivable from publicly available databases. The human CD19 antigen is for example indicated in GenBank Accession No. AAA69966.

All the specific CD19×CD3 bispecific single-chain antibodies disclosed therein, including their variants, fragments, equivalents, etc. are particularly preferred CD19×CD3 bispecific single-chain antibodies of the present invention.

As used herein, a "CD19×CD3 bispecific single-chain antibody" denotes a single polypeptide chain comprising two binding domains. Such bispecific single-chain antibodies are preferred in the context of the methods/dosage regimen of the present invention. Each binding domain comprises at least one variable region from an antibody heavy chain ("VH or H region"), wherein the VH region of the first binding domain specifically binds to CD3epsilon and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second binding domain. Such CD19×CD3 bispecific single-chain antibodies are described in great detail in WO 99/54440 and WO 2004/106381.

Preferably, the bispecific single-chain antibody applied in the methods/dosage regimen of the present invention has the domain arrangement (a) VL(CD19)-VH(CD19)-VH(CD3)-VL(CD3). However, it is also envisaged that the methods of the invention can be carried out with CD19×CD3 bispecific single-chain antibodies of other domain arrangements, such as (b) VH(CD19)-VL(CD19)-VH(CD3)-VL(CD3),
(c) VL(CD19)-VH(CD19)-VL(CD3)-VH(CD3),
(d) VH(CD19)-VL(CD19)-VL(CD3)-VH(CD3),
(e) VL(CD3)-VH(CD3)-VH(CD19)-VL(CD19),
(f) VH(CD3)-VL(CD3)-VH(CD19)-VL(CD19),
(g) VL(CD3)-VH(CD3)-VL(CD19)-VH(CD19), or
(h) VH(CD3)-VL(CD3)-VL(CD19)-VH(CD19).

A preferred CD19×CD3 bispecific single-chain antibody applied in the methods of the present invention comprises the
(a) anti-CD3 CDRs of the heavy chain shown as CD3 CDR-H1 in SEQ ID NO: 11 (RYTMH), more preferably in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or
(b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
(c) anti-CD19 CDRs of the heavy chain shown as CD19 CDR-H1 in SEQ ID NO: 17 (SYWMN), more preferably in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or
(d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19×CD3 bispecific single-chain antibody applied in the methods of the present invention comprises the CD3 CDRs of the heavy and light chain. Even more preferably, the CD19×CD3 bispecific single-chain antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues of an antibody in a consistent manner (Kabat et al., Sequences of Proteins of Immunological Interest, 1991).

Alternatively, it is preferred that the CD19×CD3 bispecific single-chain antibody applied in the methods of the present invention comprises the
(a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19×CD3 bispecific single-chain antibody applied in the methods of the present invention comprises the CD19 variable heavy and light chain and/or the CD3 variable heavy and light chain. Even more preferably, the CD19×CD3 bispecific single-chain antibody applied in the methods of the present invention comprises the CD19 variable heavy and light chain as well as the CD3 variable heavy and light chain.

In another alternative, it is also preferred that the CD19× CD3 bispecific single-chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
(d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch. *J Mol Biol.* 1970; 48:443-53; Smith and Waterman. *Adv Appl Math.* 1981; 2:482-9), which are contained in the GCG software package (Genetics Computer Group, 575 Science Drive, Madison, Wis., USA 53711). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific single-chain antibodies described herein (preferably Blinatumomab). For example, according to Crick's Wobble hypothesis, the 5' base on the anti-codon is not as spatially confined as the other two bases, and could thus have non-standard base pairing. In other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick. *J Mol Biol.* 1966; 19:548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19×CD3 bispecific single-chain antibodies described herein. Cytotoxic activity of the CD19× CD3 bispecific single-chain antibody or an antibody construct having e.g. 70%, 80%, 90%, 95%, 96%, 97%, 98% or 99% sequence identity to the amino acid sequences of the CD19×CD3 bispecific single-chain antibodies described herein can be determined by methods as illustrated, e.g. in WO 99/54440.

It is particularly preferred, that said CD19×CD3 bispecific single-chain antibody has the amino acid sequence shown in SEQ ID NO: 1. Also particularly preferred is the CD19× CD3 bispecific single-chain antibody as described in WO 99/54440 as well as those CD19×CD3 bispecific single-chain antibodies described in WO 2004/106381 and WO 2008/119565. Blinatumomab (or AMG 103 or MT103) is most preferred. It also preferred that the bispecific single-chain antibody that is applied in the context of the present invention has an N- and/or C-terminal tag, preferably a C-terminal tag. A preferred example of a C-terminal tag is a His-tag. Said His-tag comprises or consists of six histidine residues in length. It is even more preferred that said His-tag is six histidine residues in length and is located at the C-terminus of the CD19×CD3 bispecific single-chain antibody of the present invention. Thus, in a particularly preferred embodiment of the present invention, said CD19× CD3 bispecific single-chain antibody comprises or consists of a polypeptide as represented by SEQ ID No: 1 and additionally of a hexa-histidine-tag (HHHHHH) which is located at its C-terminus. It is also preferred that the protein purification tag (His-tag being more preferred and Hexa-His-tag being most preferred) is linked to the C-terminus of said CD19×CD3 bispecific single-chain antibody of the present invention (preferably consisting of or comprising SEQ ID No: 1) via a peptide bond.

In a further preferred embodiment, said CD19×CD3 bispecific single-chain antibody including the above mentioned protein purification tag(s), His-tags being preferred and Hexa-His-tags at the C-terminus being more preferred, is produced in a host cell as defined herein. CHO is thereby a particularly preferred host cell.

In the context of the present invention "administration" or "administering" or any other grammatical form thereof means that a compound of a therapy as described herein, such as a CD3 binding domain or T-cells having a chimeric antigen receptor is in the form of a pharmaceutical composition, optionally comprising a pharmaceutically acceptable carrier. Said compound may be either the sole therapeutic agent in said pharmaceutical composition or in combination with another therapeutic agent. It is thus envisaged that the pharmaceutical composition of the present invention is employed in co-therapy approaches, i.e. in co-administration with other medicaments or drugs, for example, other medicaments for treating ALL and/or any other therapeutic agent which might be beneficial in the context of the methods of the present invention.

The administration of a pharmaceutical composition referred to herein is preferably an intravenous administration. It may be administered as a bolus injection or continually (continuously). The administration can be a bolus injection or continually or as also sometimes used herein continuously, with continually or continuously being preferred. A continual administration refers to an administration which is essentially without interruption. "Essentially without interruption" includes a continual administration usually without an uninterrupted flow or spatial extension.

By "therapeutically effective amount" is meant a dose that produces the effects for which it is administered, preferably the effect is reduction of malignant blast cells. Reduction includes the elimination of malignant blast cells or the conversion of a minimal residual disease (MRD)-positive acute lymphoblastic leukemia (ALL) status into an MRD-negative ALL status.

The attending physician and clinical factors will determine the dosage regimen. As is well known in the medical arts, dosages for any one patient depends upon many factors, including the patient's size, body surface area, age, the particular compound to be administered, sex, time and route of administration, general health status, and other drugs being administered concurrently. As is well known in the medical arts, dosages for any one patient depends upon many factors, including the adult patient's size, body surface area, age, the particular compound to be administered, sex, time and route of administration, general health status, and other drugs being administered concurrently. A typical dose can be, for example, in the ranges set forth in the embodiments of the invention and the appended examples; however, doses below or above this exemplary range are envisioned, especially considering the aforementioned factors. The exact dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. The therapeutic effect of the respective methods or method steps of the present invention is additionally detectable by all established methods and approaches which will indicate a therapeutic effect. It is, for example, envisaged that the therapeutic effect is detected by way of surgical resection or biopsy of an affected tissue/organ which is subsequently analyzed by way of immunohistochemical (IHC) or comparable immunological techniques. Alternatively it is also envisaged that the tumor markers in the serum of the patient (if present) are detected in order to diagnose whether the therapeutic approach is already effective or not. Additionally or alternatively it is also possible to evaluate the general appearance of the respective patient (fitness, well-being, decrease of tumor-mediated ailment etc.) which will also aid the skilled practitioner to evaluate whether a therapeutic effect is already there. The skilled person is aware of numerous other ways which will enable him or her to observe a therapeutic effect of the compounds of the present invention.

The term "treatment" as used herein means in the broadest sense medical procedures or applications that are intended to relieve illness. In the present case, the application of a therapy which comprises re-directing of T-cells against target cells as described herein is for the treatment, amelioration or elimination of the ALL disease in subjects.

The term "amelioration" as used herein is synonymous with improvement. If a subject suffering from ALL shows amelioration, the subject is clearly better—there is some improvement in her or his condition. For example, it may be an improvement in the ALL subject's condition, if a stabilization of the ALL disease can be achieved (also termed stable disease), i.e. the ALL disease is no longer progressive. Even better, MRD positive acute lymphoblastic leukemia (ALL) is converted into an MRD negative status.

The term "elimination" as used herein means the removal of leukemic cells from the body of an ALL subject.

As mentioned above, the present inventors found that the amount of blast cells per 200 counted bone marrow cells in a bone marrow sample and/or the number of blast cells in a CSF sample from a subject can be used as risk-stratification markers for a risk management of subjects suffering from B-precursor ALL and which are intended for a therapy comprising re-directing T cells.

Accordingly, in a further aspect the present invention relates to a use of a bone marrow sample from a subject suspected to or having B-precursor ALL for predicting the risk of developing a potential adverse neurological reaction, wherein an amount of at least 20% blast cells per 200 counted bone marrow cells in a bone marrow sample of said subject is indicative for a reduced or no risk of a potential adverse neurological reaction for said subject.

Also, the present invention provides a use of a CSF sample from a subject suspected to have or having B-precursor ALL for predicting the risk of developing a potential adverse neurological reaction, wherein 5 or less blast cells per 1 µl in a CSF sample from said subject is indicative for a reduced or no risk of a potential adverse neurological reaction for said subject.

Moreover, the present invention relates in yet another aspect to a use of the amount of blast cells in a bone marrow sample of a subject suspected or having B-precursor ALL for predicting the risk of developing a potential adverse neurological reaction, wherein an amount of at least 20% blast cells per 200 counted bone marrow cells in a bone marrow sample of said subject is indicative for a reduced or no risk of a potential adverse neurological reaction for said subject.

The present invention also encompasses a use of the number of blast cells in a CSF sample of a subject suspected to have or having B-precursor ALL for predicting the risk of developing a potential adverse neurological reaction, wherein a number of 5 or less blast cells per 1 µl in a CSF sample of said subject is indicative for a reduced or no risk of a potential adverse neurological reaction for said subject.

Furthermore, the present invention provides a method for predicting the risk of developing a potential adverse neurological reaction of a subject having B-precursor ALL, comprising determining the amount of blast cells in a bone marrow sample from a subject, wherein an amount of at least 20% blast cells per 200 counted bone marrow cells in a bone marrow sample of said subject is indicative for a reduced or no risk of a potential adverse neurological reaction for said subject.

Similarly, the present invention provides a method for predicting the risk of developing a potential adverse neurological reaction of a subject having B-precursor ALL, comprising determining the number of blast cells in a CSF sample from a subject, wherein a number of 5 or less blast cells per 1 µl in a CSF sample of said subject is indicative for a reduced or no risk of a potential adverse neurological reaction for said subject.

In accordance with the present invention by the term "sample" is intended any biological sample obtained from a human patient containing polynucleotides or polypeptides or portions thereof. Biological samples include body fluids (such as blood, serum, plasma, urine, saliva, synovial fluid and spinal fluid) and tissue sources found to malignant CD19 positive lymphocytes. Methods for obtaining tissue biopsies and body fluids from patients are well known in the art. Generally, a biological sample which includes peripheral blood mononuclear cells (PBMCs), in particular B cells and T cells is preferred as a source.
A sample which includes peripheral blood mononuclear cells (PBMCs), in particular B cells and T cells is preferably taken from peripheral blood of a human patient.
Other preferred samples are whole blood, serum, plasma or synovial fluid, with plasma or serum being most preferred. However, a sample from peripheral blood of a human patient is particularly preferred.
A more preferred sample applied in the methods and uses of the present invention is a bone marrow sample from a subject and/or a CSF sample from a subject. The skilled person knows how to obtain such samples.

The amount of blast cells in a bone marrow sample is determined by means and methods known in the art, preferably in accordance with the teaching of the text book "Hematopathology" Faramarz Naeim, P. Nagesh Rao, Wayne W. Grody, Academic Press, Elsevier, 2008, particularly in accordance with the teaching in Chaper 1, page 5, "Bone Marrow Examintion"—"Bone marrow smears". As taught therein, at least 200 cells are counted by randomly selected areas of a properly stained and adequately cellular marrow smear to calculate the differential count. In the context of the present invention in particular blast cells in a bone marrow sample are counted and their amount is determined per 200 counted bone marrow cells.

The number of blast cells in a CSF sample determined by means and methods known in the art. Typically, cells within 1 µl of a CSF sample are appropriately stained in order to make eventually present blast cells visible and distinguishable from other cells and the total number of blast cells is counted.

The present invention furthermore provides a kit comprising a CD3 binding domain and instructions indicating that
(i) an amount of at least 20% blast cells per 200 counted bone marrow cells in a bone marrow sample from said subject is indicative for a reduced or no risk of a potential adverse neurological reaction for said subject when being subjected to a therapy which comprises re-directing of T-cells against target cells;
(ii) wherein a number of 5 or less blast cells per 1 µl in a CSF sample from said subject is indicative for a reduced or no risk of a potential adverse neurological reaction for said subject when being subjected to a therapy which comprises re-directing of T-cells against target cells;
(iii) wherein an amount of about less than 20% blast cells per 200 counted bone marrow cells in a bone marrow sample, while concomitantly a number of 5 or less blast cells per 1 µl in a CSF sample from said subject is indicative for a reduced or no risk of a potential adverse neurological reaction for said subject when being subjected to a therapy which comprises re-directing of T-cells against target cells;
(iv) wherein an amount of about less than 20% blast cells per 200 counted bone marrow cells in a bone marrow sample from said subject is indicative for an increased risk of a potential adverse neurological reaction for said subject when being subjected to a therapy which comprises re-directing of T-cells against target cells;
(v) wherein a number of more than 5 blast cells per 1 µl in a CSF sample from said subject is indicative for an increased risk of a potential adverse neurological reaction for said subject when being subjected to a therapy which comprises re-directing of T-cells against target cells;
(vi) wherein an amount of about less than 20% blast cells per 200 counted bone marrow cells in a bone marrow sample, while concomitantly a number of more than 5 blast cells per 1 µl in a CSF sample from said subject is indicative for an increased risk of a potential adverse neurological reaction for said subject when being subjected to a therapy which comprises re-directing of T-cells against target cells.

Said kit is preferably a pharmaceutical kit. Said kit may preferably further comprise means for administering said CD3 binding domain, such as a syringe, an infusion bag, a pump, and the like.

Examples

Data from three clinical trials MT103-206, MT103-211 and MT103-205 aiming at the treatment of B-precursor ALL were collected and analysed.

| Trial | Indication | Dose | Patient number |
|---|---|---|---|
| MT103-206 | Relapsed/refractory adult B-precursor ALL | 5 µ/m²/d; 5-15 µ/m²/d; 5-15-30 µ/m²/d | 36 |
| MT103-211 | Relapsed/refractory adult B-precursor ALL | 9-28 µ/m²/d | 61 |
| MT103-205 | Relapsed/refractory pediatric B-precursor ALL | 5 µ/m²/d; 15 µ/m²/d; 30 µ/m²/d; 15-30 µ/m²/d; 5-15 µ/m²/d | >50 |

| Amount of blast cells in bone marrow per 200 counted cells | Adverse events |
|---|---|
| 5% MT103-206 | 22% (8 of 36) |
| 10% MT103-211 | 12% (23 of 189) |
| 20% MT103-205 | <2.5% (1 of > 50) |

| | 14-6.1.5.1.3 Incidence of TEAEs of at least CTC grade 3/at least severe related to study medication by MedDRA SOC and PT - by actual dose received | | | | | | | | | | | | | | |
|---|---|---|---|---|---|---|---|---|---|---|---|---|---|---|---|
| MedDRA System Organ Class Preferred Term | 5 µg/m²/d (N = 3) | | | 15 µg/m²/d (N = 7) | | | 5/15 µg/m²/d (N = 21) | | | 5/15/30 µg/m²/d (N = 5) | | | Overall (N = 36) | | |
| | AE n | Pat. n | Pat. % | AE n | Pat. n | Pat. % | AE n | Pat. n | Pat. % | AE n | Pat. n | Pat. % | AE n | Pat. n | Pat. % |
| TOTAL | 7 | 2 | (66.7%) | 30 | 7 | (100.0%) | 31 | 11 | (52.4%) | 6 | 3 | (60.0%) | 74 | 23 | (63.9%) |
| Infections and infestations | 1 | 1 | (33.3%) | 1 | 1 | (14.3%) | 0 | 0 | (0.0%) | 0 | 0 | (0.0%) | 2 | 2 | (5.6%) |
| Central nervous system infection | 1 | 1 | (33.3%) | 0 | 0 | (0.0%) | 0 | 0 | (0.0%) | 0 | 0 | (0.0%) | 1 | 1 | (2.8%) |
| Sinusitis | 0 | 0 | (0.0%) | 1 | 1 | (14.3%) | 0 | 0 | (0.0%) | 0 | 0 | (0.0%) | 1 | 1 | (2.8%) |
| Blood and lymphatic system disorders | 1 | 1 | (33.3%) | 8 | 6 | (85.7%) | 7 | 5 | (23.8%) | 1 | 1 | (20.0%) | 17 | 13 | (36.1%) |
| Leukopenia | 0 | 0 | (0.0%) | 3 | 2 | (28.6%) | 3 | 2 | (9.5%) | 1 | 1 | (20.0%) | 7 | 5 | (13.9%) |
| Lymphopenia | 0 | 0 | (0.0%) | 3 | 3 | (42.9%) | 0 | 0 | (0.0%) | 0 | 0 | (0.0%) | 3 | 3 | (8.3%) |
| Thrombocytopenia | 1 | 1 | (33.3%) | 1 | 1 | (14.3%) | 1 | 1 | (4.8%) | 0 | 0 | (0.0%) | 3 | 3 | (8.3%) |
| Anaemia | 0 | 0 | (0.0%) | 0 | 0 | (0.0%) | 1 | 1 | (4.8%) | 0 | 0 | (0.0%) | 1 | 1 | (2.8%) |
| Disseminated intravascular coagulation | 0 | 0 | (0.0%) | 1 | 1 | (14.3%) | 0 | 0 | (0.0%) | 0 | 0 | (0.0%) | 1 | 1 | (2.8%) |
| Neutropenia | 0 | 0 | (0.0%) | 0 | 0 | (0.0%) | 1 | 1 | (4.8%) | 0 | 0 | (0.0%) | 1 | 1 | (2.8%) |
| Pancytopenia | 0 | 0 | (0.0%) | 0 | 0 | (0.0%) | 1 | 1 | (4.8%) | 0 | 0 | (0.0%) | 1 | 1 | (2.8%) |
| Immune system disorders | 0 | 0 | (0.0%) | 1 | 1 | (14.3%) | 1 | 1 | (4.8%) | 0 | 0 | (0.0%) | 2 | 2 | (5.6%) |
| Cytokine release syndrome | 0 | 0 | (0.0%) | 1 | 1 | (14.3%) | 1 | 1 | (4.8%) | 0 | 0 | (0.0%) | 2 | 2 | (5.6%) |
| Metabolism and nutrition disorders | 0 | 0 | (0.0%) | 1 | 1 | (14.3%) | 1 | 1 | (4.8%) | 0 | 0 | (0.0%) | 2 | 2 | (5.6%) |
| Tumour lysis syndrome | 0 | 0 | (0.0%) | 1 | 1 | (14.3%) | 1 | 1 | (4.8%) | 0 | 0 | (0.0%) | 2 | 2 | (5.6%) |
| Psychiatric disorders | 0 | 0 | (0.0%) | 1 | 1 | (14.3%) | 0 | 0 | (0.0%) | 0 | 0 | (0.0%) | 1 | 1 | (2.8%) |
| Disorientation | 0 | 0 | (0.0%) | 1 | 1 | (14.3%) | 0 | 0 | (0.0%) | 0 | 0 | (0.0%) | 1 | 1 | (2.8%) |
| Nervous system disorders | 5 | 2 | (66.7%) | 3 | 1 | (14.3%) | 6 | 3 | (14.3%) | 2 | 2 | (40.0%) | 16 | 8 | (22.2%) |
| Encephalopathy | 2 | 1 | (33.3%) | 3 | 1 | (14.3%) | 0 | 0 | (0.0%) | 1 | 1 | (20.0%) | 6 | 3 | (8.3%) |
| Tremor | 0 | 0 | (0.0%) | 0 | 0 | (0.0%) | 2 | 2 | (9.5%) | 1 | 1 | (20.0%) | 3 | 3 | (8.3%) |
| Aphasia | 0 | 0 | (0.0%) | 0 | 0 | (0.0%) | 1 | 1 | (4.8%) | 0 | 0 | (0.0%) | 1 | 1 | (2.8%) |
| Apraxia | 1 | 1 | (33.3%) | 0 | 0 | (0.0%) | 0 | 0 | (0.0%) | 0 | 0 | (0.0%) | 1 | 1 | (2.8%) |

The invention claimed is:

1. A method of treating B-precursor acute lymphoblastic leukemia (ALL) in a subject determined to be at a reduced risk for developing a potential adverse neurological reaction from a therapy which comprises re-directing of T-cells against target cells, comprising selecting said subject for having a reduced risk when the subject has been determined as having
   at least 20% blast cells per 200 counted bone marrow cells in a bone marrow sample; and
   administering to said subject determined to be at a reduced risk said therapy which comprises re-directing of T-cells against target cells.

2. The method of claim 1, wherein the neurological reaction is one or more selected from the group consisting of: confusion, ataxia, disorientation, dysphasia, aphasia, speech impairment, cerebellar symptoms, tremor, apraxia, seizure, grand mal convulsion, palsy, and balance disorder.

3. The method of claim 1, wherein said therapy which comprises re-directing of T-cells against target cells in a subject, includes a CD3 binding domain.

4. The method of claim 3, wherein said CD3 binding domain is part of a bispecific single chain antibody.

5. The method of claim 4, wherein said bispecific single chain antibody is a CD19×CD3 bispecific single chain antibody.

6. The method of claim 5, wherein said CD19×CD3 bispecific single chain antibody is blinatumomab (AMG 103).

7. The method of claim 1, wherein said therapy includes a genetically engineered T-cell having a chimeric antigen receptor (CAR).

8. The method of claim 1, wherein said subject is a human.

* * * * *